US006814075B2

(12) United States Patent
Boussignac

(10) Patent No.: US 6,814,075 B2
(45) Date of Patent: Nov. 9, 2004

(54) RESPIRATORY ASSISTANCE DEVICE

(76) Inventor: Georges Boussignac, 1, Avenue de Provence, 92160 Antony (FR)

( * ) Notice: Subject to any disclaimer, the term of this patent is extended or adjusted under 35 U.S.C. 154(b) by 0 days.

(21) Appl. No.: 10/451,659

(22) PCT Filed: Nov. 5, 2002

(86) PCT No.: PCT/FR02/03779
§ 371 (c)(1),
(2), (4) Date: Jun. 25, 2003

(87) PCT Pub. No.: WO03/039638
PCT Pub. Date: May 15, 2003

(65) Prior Publication Data
US 2004/0050389 A1 Mar. 18, 2004

(30) Foreign Application Priority Data
Nov. 6, 2001 (FR) .......................................... 01/14318

(51) Int. Cl.[7] .............................................. A61M 16/00
(52) U.S. Cl. ............................ 128/204.24; 128/204.25; 128/205.11; 128/204.22; 128/204.18
(58) Field of Search ....................... 128/205.11, 204.24, 128/204.25, 204.22, 911, 912, 207.16, 204.18

(56) References Cited

U.S. PATENT DOCUMENTS

| 3,542,020 | A | * | 11/1970 | Bushman ..................... 137/803 |
| 3,661,528 | A | * | 5/1972 | Falk .......................... 73/863.01 |
| 3,850,171 | A | * | 11/1974 | Ball et al. .................. 128/204.25 |
| 3,853,105 | A | * | 12/1974 | Kenagy ..................... 128/204.25 |
| 3,881,480 | A | * | 5/1975 | Lafourcade ................ 128/200.21 |
| 3,906,996 | A | * | 9/1975 | DePass et al. .............. 137/893 |
| 3,913,607 | A | | 10/1975 | Price |
| 4,022,219 | A | * | 5/1977 | Basta ....................... 128/207.14 |
| 4,207,884 | A | * | 6/1980 | Isaacson .................. 128/200.24 |
| 4,558,708 | A | * | 12/1985 | Labuda et al. ............. 600/532 |
| 4,848,333 | A | * | 7/1989 | Waite ...................... 128/205.11 |
| 4,852,583 | A | * | 8/1989 | Walker ..................... 600/529 |
| 5,372,129 | A | * | 12/1994 | Ryder ...................... 128/205.11 |
| 5,538,002 | A | | 7/1996 | Boussignac et al. |
| 5,544,648 | A | * | 8/1996 | Fischer, Jr. ............... 128/207.14 |
| 5,789,660 | A | * | 8/1998 | Kofoed et al. .............. 73/23.2 |
| 6,152,132 | A | * | 11/2000 | Psaros .................... 128/204.25 |
| 6,273,087 | B1 | * | 8/2001 | Boussignac et al. ...... 128/204.22 |
| 6,516,801 | B2 | * | 2/2003 | Boussignac .............. 128/204.24 |

FOREIGN PATENT DOCUMENTS

GB          550725          1/1943

OTHER PUBLICATIONS

International Search Report dated Mar. 26, 2003.

* cited by examiner

Primary Examiner—Henry Bennett
Assistant Examiner—Mital Patel
(74) Attorney, Agent, or Firm—Stevens, Davis, Miller & Mosher, LLP

(57) ABSTRACT

A respiratory assistance device may include a tube that forms a main channel for connecting a distal end of the tube to a respiratory airway of a patient, such that the main channel connects the respiratory system of the patient to the outside. The device may also include an auxiliary channel, for connecting to a source of breathable gas to blow a ventilating gas stream into the patient's respiratory system. This auxiliary channel emerges in the main channel by a distal orifice arranged in front of a distal end of the main channel. A deflecting device may be provided, facing the distal orifice of the auxiliary channel, for deflecting the ventilating breathable gas stream toward the axis of the main channel. Also, a communication device, between the deflecting device and the distal end of the main channel, may be included for opening and closing a passageway.

5 Claims, 3 Drawing Sheets

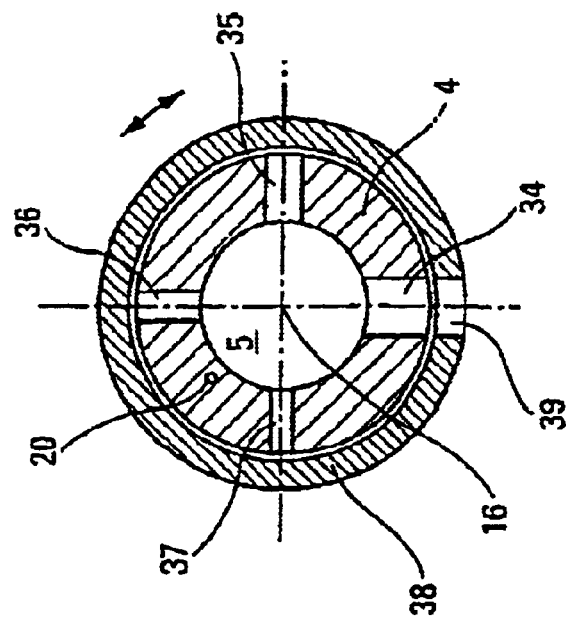
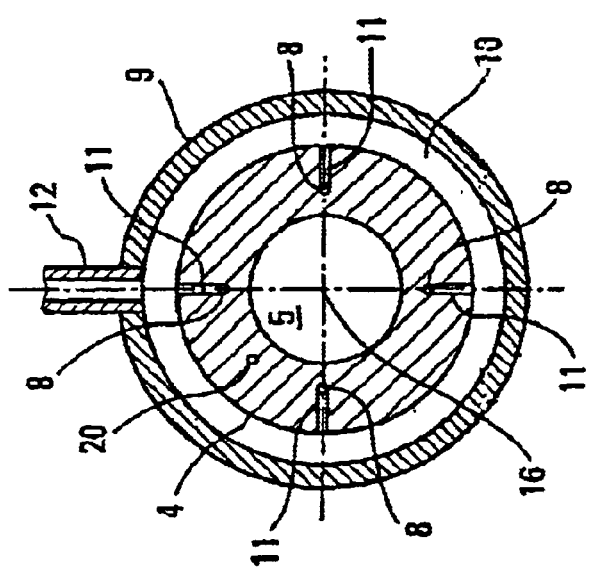
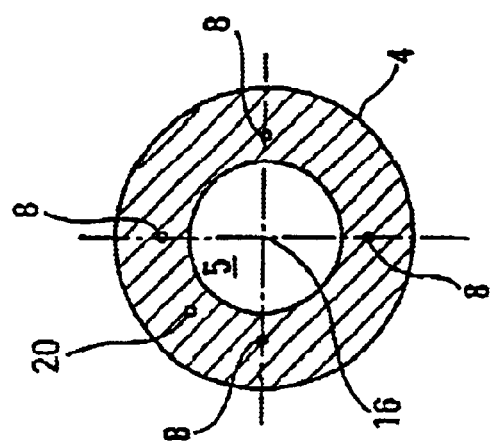

RESPIRATORY ASSISTANCE DEVICE

FIELD OF THE INVENTION

The subject of the invention is a respiratory assistance device which can be used on patients whose spontaneous respiration is absent or insufficient, whether or not they are placed under artificial respiration.

BACKGROUND OF THE RELATED ART

Various devices are known, such as masks, oral, nasal, endotracheal or tracheotomic catheters or cannulae, designed to form the junction between an artificial and/or anaesthetic respiration apparatus and the respiratory system of a patient. These devices, essentially in the form of tubes, may, according to need, comprise immobilizing means, such as lugs or flanges close to the proximal end, for holding them over the patient's mouth or nose, or else inflatable cuffs close to the distal end, for holding them by friction in the trachea.

Known devices have significant drawbacks. Thus, for example, when a tube of known type is disconnected from the artificial respirator and the patient needs oxygen-enriched air it is necessary to insert a catheter connected to an oxygen source into said tube. Moreover, in the case of insufficient spontaneous respiration, the patient must necessarily remain connected to the respirator until the complete reestablishment of his spontaneous respiration.

Therefore, in order to overcome these drawbacks, respiratory assistance devices have already been proposed, for example in documents EP-A-0 390 684, EP-A-0 701 834 and EP-A-0 978 291, which devices, apart from the main channel formed by the tube, comprise at least one auxiliary channel, for example made in the wall of said tube, allowing a stream of breathable gas to be injected for the patient's ventilation, this auxiliary channel emerging in the main channel in front of the distal end thereof.

In these devices, the breathable gas feeding the auxiliary channel is usually pure oxygen. However, some patients, whose body is used to a high level of blood carbon dioxide, are not able to withstand ventilation with pure oxygen, which would lead to a risk of a mild heart attack.

SUMMARY OF THE INVENTION

The object of the present invention is to improve the respiratory assistance devices summarized above in order to allow them to take the situation of these latter patients into account.

To this end, according to the invention, the respiratory assistance device comprising a tube which forms a main channel and which is designed to be connected by its distal portion to a respiratory airway of a patient such that said main channel connects the respiratory system of said patient to the outside, said device further comprising at least one auxiliary channel connected to a source of breathable gas in order to be able to blow a stream of such a breathable gas into said respiratory system and emerging in said main channel by at least one distal orifice arranged in front of the distal end of the latter, is noteworthy in that it comprises, between said orifice of said auxiliary channel and said distal end of said main channel, communication means which can be opened and closed and, when open, are capable of forming a passage connecting said main channel to the external environment.

Thus, by virtue of the present invention, when said communication means are open, external air is sucked through them via said breathable gas stream, the air thus introduced diluting said breathable gas that can then be tolerated by the patient whose situation has been summarized above.

Preferably, so that the device can be adapted to all circumstances and to all patients, it is advantageous that said passage connecting said main channel to the environment has a variable cross section. Thus, it is possible to adjust the dilution of the breathable gas by the ambient air in an optimum manner.

In one practical embodiment of said communication means, the latter are of the type with a sideways-drilled rotary ring capable of uncovering passages of different diameters. Such a ring may be mounted directly on said tube or else on a funnel in communication with said main channel.

It is advantageous that, facing the distal orifice of said auxiliary channel, means for deflecting said ventilating breathable gas stream toward the axis of said channel be provided and that said communication means be placed between said deflecting means and said distal end of the main channel. This is because, in this case, said deflecting means create, in said main channel, a vacuum that enhances suction of the ambient air through said communication means.

BRIEF DESCRIPTION OF THE DRAWINGS

The figures of the appended drawing will make it easier to understand how the invention can be produced. In those figures, identical references denote similar elements.

FIGS. 2, 3, and 4 are cross sections along the lines II—II, III—III, and IV—IV, respectively, of FIG. 1.

DETAILED DESCRIPTION OF THE INVENTION

Figure 1:
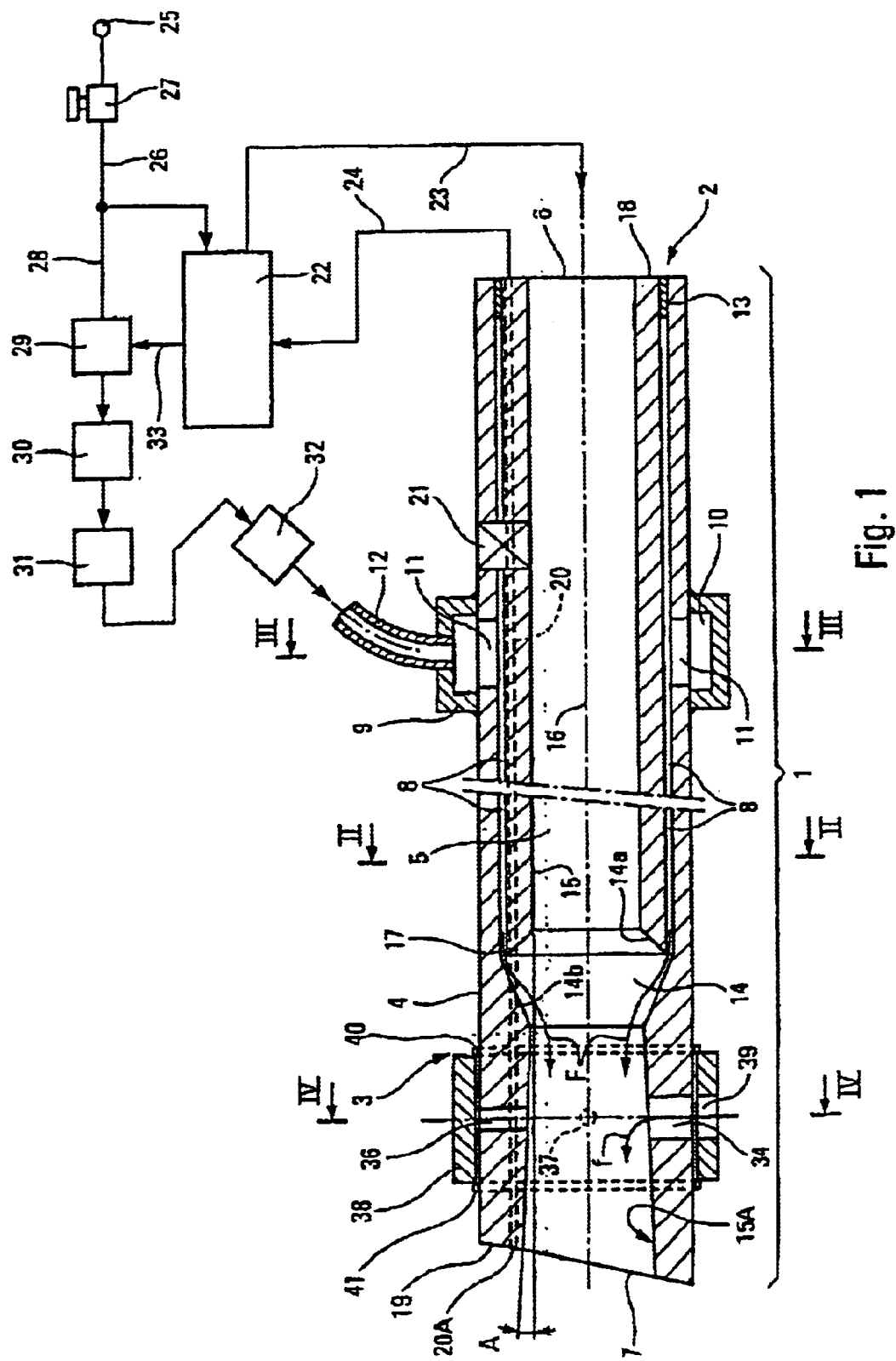
FIG. 1 is a schematic and partial view, in enlarged axial section, of one embodiment of a device of the invention.

FIG. 1 shows, schematically and on a large scale, only the proximal 2 and distal 3 portions of one embodiment 1 of the device according to the invention. This embodiment may constitute, for example, an oronasal endotracheal catheter with or without a cuff, a pediatric endotracheal catheter, a gas-monitoring catheter, an endobronchial catheter, a nasopharyngeal catheter, an anatomical intubation catheter for a child, a neonatal Cole catheter, a Gedel cannula catheter, an oxygen therapy nasal catheter, a nasal or buc-conasal mask or a nasal balloon for treating sleep apnea.

The device 1 comprises a tube 4 which is flexible or preformed (in order to match the morphology of the patient), defining a main channel 5 having a proximal orifice 6 and a distal orifice 7 at the ends of said tube, respectively.

Thus, the main channel 5 is capable of providing the passage between the orifices 6 and 7, one (the orifice 7) of which is designed to be placed inside the respiratory airways of a patient, and the other (the orifice 6) of which is designed to be placed outside said patient. This orifice 6 may emerge outside and, in such a case, the patient may inhale fresh air and exhale contaminated air through the main channel 5. It is also possible, as is explained hereinbelow, to connect the orifice 6 to a source of pressurized breathable gas and to provide a system of unidirectional valves, such that the patient inhales the breathable gas from said source through said main channel 5 and exhales the contaminated gas to the outside, also through this main channel.

The diameter of the main channel 5 is of the order of a few millimeters. Satisfactory tests were carried out with diameters of 3 mm, 7 mm, 8 mm, and 12 mm.

Moreover, auxiliary channels 8 are made within the thickness of the wall of the tube 4, the channels extending over practically the entire length of the main channel and being designed to be connected to a source of pressurized breathable gas, as is described hereinbelow.

The source of pressurized breathable gas may be connected by means of a ring 9, surrounding the tube 4 in a sealed manner, on the same side as the proximal end 2, and defining a sealed annular chamber 10 around said tube. The auxiliary channels 8 are placed in communication with the chamber 10, using local cutaways 11 in the wall of the tube 4, and said chamber 10 is connected to said source of breathable air via a pipe 12. Of course, the proximal ends of the channels 8 are closed off, for example by stoppers 13 inserted from the proximal end face 18 of the tube 4.

The auxiliary channels 8 have a smaller diameter than that of the main channel 5. The diameter of the auxiliary channels 8 is preferably less than 1 mm and, advantageously, it is about 400 to 800 microns. On the distal side, the auxiliary channels 8 emerge in a recess 14 of the inner wall 15 of the tube 4. The recess 14 is annular and centered on the axis 16 of said tube. It comprises a face 14a which is substantially transverse or slightly inclined so as to form a flare in the main channel 5 into which said auxiliary channels 8 emerge via their orifices 17, and a face 14b following on from the face 14a and converging in the direction of the axis 16.

Preferably, between the convergent inclined face 14b and the distal orifice 7, the inner wall 15 has a part 15A which is slightly flared outward, as is illustrated by the angle A in FIG. 1.

Thus, when the auxiliary channels 8 are fed with pressurized breathable gas through the elements 9 through 12, the corresponding gas streams come up against the inclined face 14b, which deflects them in the direction of the axis 16 (arrows F in FIG. 1), causing a region of vacuum in the vicinity of the latter, enhancing the gas flow inside the main channel 5, from the proximal orifice toward the distal orifice.

Thus the patient's inspiration is enhanced.

Preferably, the distance between each of the orifices 17 and the orifice 7 is about 1 to 2 cm.

At least one additional channel 20 is provided within the thickness of the tube 4 so as to emerge at 20A in the vicinity of the distal end 19 of the tube 4 and to act as a pressure take-off.

As a safety measure, a calibrated exhaust valve 21 may be provided in the proximal end 2 of the tube 4. Thus, in the event of accidental overpressure in the main channel 5, a leakage of gas occurs outside the patient, through the wall of the tube 4, in order to eliminate this overpressure instantaneously.

As shown in FIGS. 2 and 3, the auxiliary channels 8 are arranged regularly around the axis of the tube 4. They vary in number depending on use (adult or child), but there are generally between 3 and 9. Furthermore, at least one of the auxiliary channels 8 may be specially adapted to provide a medical fluid.

The tube 4 of the device according to the invention may be made from any material already used in respiratory catheters, for example, a polyvinyl chloride, with an optional silicone coating, or from steel to allow high-pressure injections.

Of course, the dimensions of the device according to the invention may be very variable, essentially depending on the airway in which the tube is placed and on the size of the patient, who may be an adult, a child, or a new-born or premature baby.

The device 1 further comprises a feed and control device 22 that is respectively connected to the orifice 6 of the proximal end 2 of the tube 4 by means of a link 23 and to the additional channel 20 by means of a link 24.

The feed and control device 22 is fed with pressurized breathable gas, for example pure oxygen, by a source 25, to which it is connected by a pipe 26 on which an adjustable flow meter-pressure regulator 27 is mounted.

The outlet from the flow meter-pressure regulator 27 is connected to the pipe 12 via a branch pipe 28 on which a controlable valve 29, an adjustable pressure-drop device 30 limiting flow rate and pressure (for example a tube with a calibrated pipe), a humidifier 31 and a calibrated exhaust valve 32, with adjustable calibration, are mounted in series. The controlable valve 29 is controlled by the feed and control device 22 via a link 33.

By way of nonlimiting example, the flow meter-pressure regulator 27 may deliver, into the pipe 28, the breathable gas coming from the source 25 at a pressure P, for example equal to 3.5 bar with a maximum adjustable flow rate of, for example, 32 liters per minute, while the flow rate and pressure limiter 30, receiving this breathable gas from the pipe 28, may reduce the pressure thereof down to a value p, for example equal to 0.5 bar (for an adult) and to 0.07 bar (for a child), and the flow rate down to a value d, for example equal to 0.5 liters per minute. As for the exhaust valve 32, this is calibrated to the pressure p.

Moreover (see FIGS. 1 and 4), between the annular recess 14 and the distal orifice 7, the wall of the tube 4 is drilled by through-holes 34 to 37 that have different diameters and have distributed around the axis 16. The holes 34 to 37 are covered by a ring 38, capable of rotating with gentle friction around said tube 4 and itself provided with a hole 39 which can be placed opposite one or other of the holes 34 to 37 by rotating the ring 38. The hole 39 has a diameter at least equal to that of the hole 34, which is the largest of the holes 34 to 37. The ring 38 is trapped on the tube 4, by means of annular side ribs 40 and 41.

As can be seen in FIG. 4, the ring 38 may take either at least one position in which it closes off all the holes 34 to 37, or positions in which the hole 39 is aligned with each of the holes 34 to 37, respectively. In these latter cases, on each occasion, a passage is established between the main channel 5 and the external environment, through the corresponding hole 34 to 37. Of course, the cross section of such a passage is then determined by the cross section of the hole 34 to 37 in question.

The operating modes of the device 1 according to the invention are as follows:

in the artificial respiration mode, the ring 38 closes off all the holes 34 to 37 and the feed and control device 22, on the one hand, closes the valve 29 via the link 33, such that the pipe 12 is not fed with gas and, on the other hand, directs the breathable gas into the tube 4 via the link 23. This device 22 comprises means (not shown) for adjusting the pressure and the flow rate of the breathable gas that it receives from the pipe 26 and that it directs to the tube 4. If an overpressure occurs in the respiratory airway of the patient, it is detected and transmitted, via the additional channel 20 and the link 24, to the device 22, which stops its operation. Furthermore, if this overpressure exceeds the calibration threshold of the calibrated valve 21, for example if the additional channel 20 is obstructed by mucus and is not able to transmit the overpressure information to the device 22, this valve 21 opens and the proximal channel 5 is opened to the atmosphere;

in the respiratory assistance mode, the feed and control device 22 cuts the link 23 in order to place the orifice 6 in communication with the atmosphere and controls the valve 29 via the link 33 so that the latter directs a continuous or pulsed stream of breathable gas to the patient through the limiter 30, the humidifier 31, the calibrated exhaust valve 32, and the auxiliary channels 8. Moreover, the ring 38 is rotated in order to bring the hole 39 opposite one of the holes 34 through 37, such that communication is made between the main channel 5 and the external environment, downstream of the annular recess 14, where a region of vacuum is generated by the gas streams coming out of the auxiliary channels 8. Next, external air is sucked through said communication (see arrow f) and mixed with said gas streams, and is thus diluted. Of course, the dilution rate of these gas streams depends on which hole 34 through 37 they pass through. It may be noted that, for constant injection conditions of said streams, the dilution rate corresponding to each of the holes 34 through 37 may be calibrated once and for all, such that it is possible to deliver to a patient the breathable air-gas mixture most suitable to his case by choosing the hole 34 through 37 opposite which the hole 39 of the ring 38 will be brought. If an overpressure occurs in the respiratory airway of the patient, as was described above, this overpressure is detected and transmitted by the additional channel 20, such that the device 22 closes the valve 29 and such that the pipe 28 stops directing gas to the patient. If the additional channel 20 is obstructed, the device 22 is not alerted to the overpressure in the respiratory airway of the patient and is unable to stop, but this overpressure leads to an increase in pressure in the auxiliary channels 8 and the pipe 12. When this pressure increase reaches the opening threshold of the safety valve 32, the latter opens and the breathable gas stream is no longer directed to the patient, but on the contrary is diverted to the outside by said safety valve 32. Thus, although in the latter case the safety system 20A, 20, 24, 22, 29 might be unable to operate, the breathable gas stream cannot reach the respiratory system of the patient.

Figure 5:
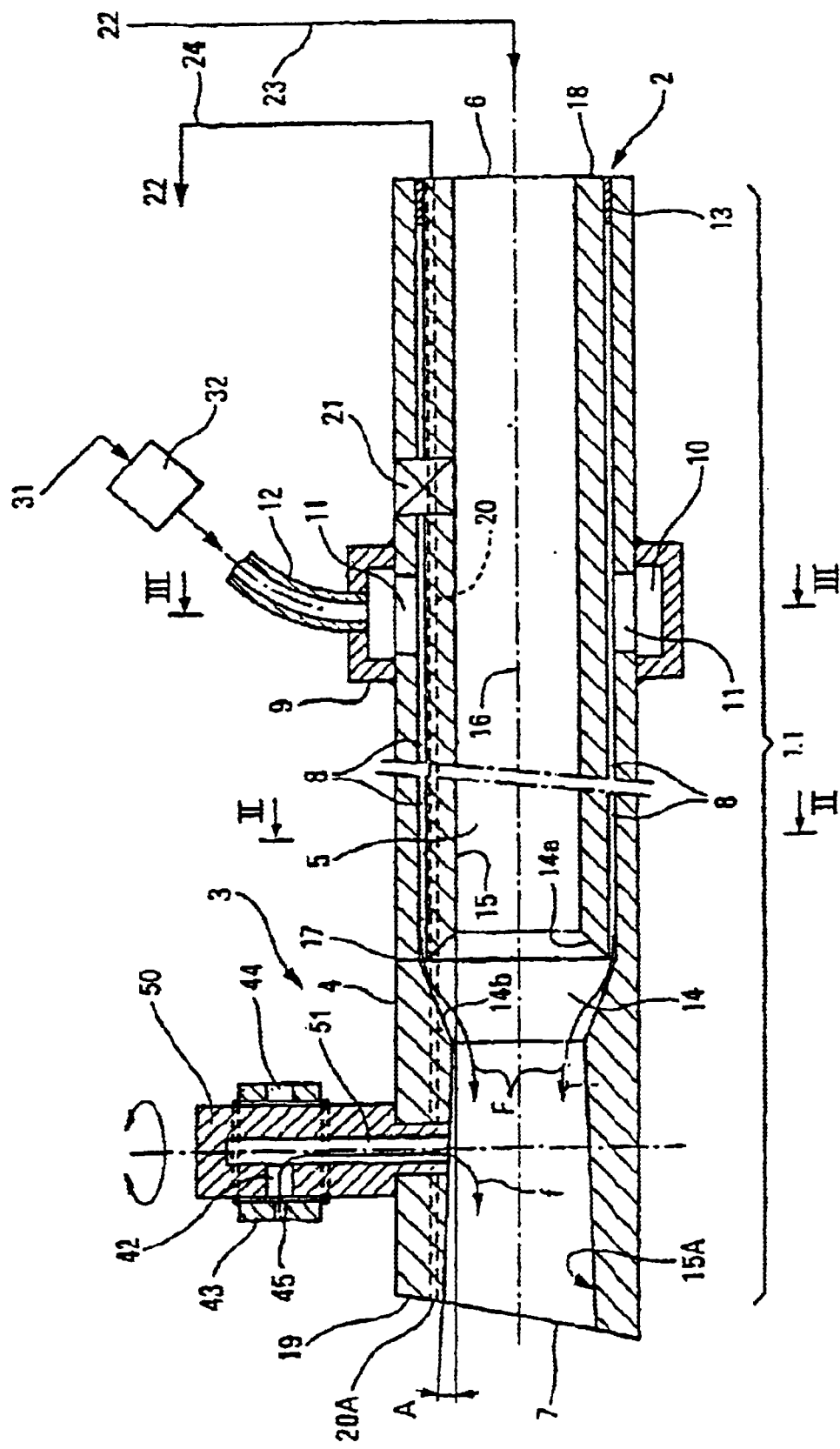
FIG. 5 shows, in a view similar to FIG. 1, a variant embodiment of the device according to the invention.

In the variant embodiment 1.1 of FIG. 5, operation is identical to that described above. In this variant embodiment, a blind funnel 50 is provided, in communication via a channel 51 with the main channel 5, said funnel being provided with a side hole 42 covered by a rotary ring 43. This latter ring is drilled with holes 44, 45 with different diameters, the largest equal to that of the hole 42, and it is able, by rotation, either to close off the hole 42, or to bring one of the holes 44, 45 opposite the hole 42.

Thus, from the foregoing, it can be seen that it is possible to dilute with air, in any desired proportion, the gas streams coming from the source 25 and passing through the auxiliary channels 8.

What is claimed is:

1. A respiratory assistance device comprising:
   a tube which forms a main channel, said tube for connecting a distal end of the tube to a respiratory airway of a patient such that said main channel connects the respiratory system of said patient to the outside;
   at least one auxiliary channel, for connecting to a source of breathable gas to blow a ventilating stream of said breathable gas into said respiratory system, that emerges in said main channel by at least one distal orifice arranged in front of a distal end of the main channel;
   deflecting means, provided facing said distal orifice of said auxiliary channel, for deflecting said ventilating breathable gas stream toward the axis of said main channel; and
   communication means, between said deflecting means and said distal end of the main channel, for opening and closing a passageway and, when said passageway is open, said communication means form a passage connecting said main channel to the external environment.

2. The device as claimed in claim 1, characterized in that the passage connecting said main channel to the environment has a variable cross section.

3. The device as claimed in claim 2, characterized in that said communication means have a sideways-drilled rotary ring capable of uncovering passages of different diameters.

4. The device as claimed in claim 3, characterized in that said rotary ring is mounted directly on said tube.

5. The device as claimed in claim 3, characterized in that said rotary ring is mounted on a funnel in communication with said main channel.

* * * * *